United States Patent [19]

White

[11] Patent Number: 4,603,212

[45] Date of Patent: Jul. 29, 1986

[54] ANALOGS OF THE ANTIBIOTIC SPECTINOMYCIN

[75] Inventor: David R. White, Kalamazoo, Mich.

[73] Assignee: The Upjohn Company, Kalamazoo, Mich.

[21] Appl. No.: 542,920

[22] Filed: Oct. 18, 1983

[51] Int. Cl.$^4$ .................. C07D 323/04; C07D 493/00
[52] U.S. Cl. ..................................................... 549/361
[58] Field of Search ......................................... 549/361

[56] References Cited

U.S. PATENT DOCUMENTS

| | | | |
|---|---|---|---|
| 3,234,092 | 2/1966 | Bergy et al. | 549/361 |
| 4,173,647 | 11/1979 | Maier et al. | 549/361 |
| 4,351,771 | 9/1982 | White | 549/361 |
| 4,361,701 | 11/1982 | White | 549/361 |

FOREIGN PATENT DOCUMENTS

| | | | |
|---|---|---|---|
| 734469 | 5/1966 | Canada | 549/361 |
| 2756912 | 7/1979 | Fed. Rep. of Germany . | |
| 2756913 | 7/1979 | Fed. Rep. of Germany . | |
| 403999 | 11/1962 | Japan | 549/361 |
| 2058062 | 4/1981 | United Kingdom | 549/361 |

OTHER PUBLICATIONS

Boissona, Adv. Org. Chem. 3, 159 (1963).
Windholz et al., Tetrahedron Lett. 8, 2555 (1967).
Danishefsky, "Siloxy Dienes in Total Synthesis" Accounts of Chemical Research, vol. 14, pp. 400–406, (1981).
McOmie, J. F., Protective Groups in Organic Chemistry, vol. 5, Plenum Press (1973).
Green, T. W., Protective Groups in Organic Synthesis, Wiley (1981).
Wiley et al., "The Chemistry of Actinospectacin. IV, The Determination of the Structure of Actinospectacin", J. Am. Chem. Soc., vol. 85, pp. 2652–2659, Sep. 5, 1963.
White et al., in "Synthesis and In Vitro Antibacterial Properties of Alkylspectinomycin Analogs", The Journal of Antibiotics, vol. XXXVI, No. 3, pp. 339–342, Mar., 1983.
March, *Advanced Organic Chemistry: Reactions, Mechanisms and Structure,* McGraw-Hill Book Company, pp. 626–636, 1968.
David et al., "Stereochimie de la Cycloaddition sur les Ethers Butadienyliques d'Alcools Chiraux. Derives en 4 et 6 de Glucosides Perbenzyles", Tetrahedron, vol. 34, pp. 299–304, 1978.
J. Amer. Chem. Soc., vol. 85, 2657 (1963).
Chem. Ber. 92, 3009, 1959.
The Journal of Antibiotics, p. 339 (1983).

*Primary Examiner*—Ethel G. Love
*Attorney, Agent, or Firm*—Joan Thierstein; Paul J. Koivuniemi

[57] ABSTRACT

The present invention relates to novel compounds and processes. In particular, the invention relates to novel analogs of the aminocyclitol antibiotic spectinomycin. More particularly, it relates to novel processes for synthesizing analogs of spectinomycin; both known analogs and the novel analogs of the present invention. Additionally, the invention includes novel intermediates.

The novel analogs of spectinomycin disclosed herein are useful as antimicrobial agents.

8 Claims, No Drawings

ANALOGS OF THE ANTIBIOTIC SPECTINOMYCIN

TECHNICAL BACKGROUND

1. Field of Invention

The present invention relates to novel compounds and processes. In particular, the invention relates to novel analogs of the aminocyclitol antibiotic spectinomycin. More particularly, it relates to novel processes for synthesizing analogs of spectinomycin; both known analogs and the novel analogs of the present invention. Additionally, the invention includes novel intermediates.

The novel analogs of spectinomycin disclosed herein are useful as antimicrobial agents.

Spectinomycin is the compound illustrated, with numbering of carbon positions in formula $I_1$.

The present invention relates to novel C-6' analogs, including novel analogs of the 5'-desmethyl analog, of spectinomycin illustrated in formula I' wherein $E'_1$ and $E'_2$ may be the same or different, and are as follows:

(a) $E'_1$ is hydrogen and $E'_2$ is aryl or an essentially hydrocarbyl substituent with the proviso that the hydrocarbyl may not be aminoalkyl, hydroxy alkyl, alkoxy alkyl, and that when the substituent is haloalkyl then at least one halo atom is on a carbon of the alkyl other than the terminal carbon.

(b) $E'_1$ and $E'_2$ are the same or different and are selected from the group consisting of hydrogen and $C(O)OR'_2$ wherein $R'_2$ is hydrogen, alkyl of from 1 to 8 carbon atoms, inclusive, or aryl, with the proviso that $E'_1$ and $E'_2$ cannot both be hydrogen or (c) $E'_1$ and $E'_2$ are the same or different and are hydrogen or CN with the proviso that $E'_1$ and $E'_2$ cannot both be hydrogen.

The present invention also relates to novel analogs of C-6' analogs (formula I') in which the hydrogen atoms attached to each of the nitrogen atoms bonded to C-1 and C-3 (analogous to the numbering of carbon positions illustrated in formula $I_1$) in the molecules are replaced by a blocking group, i.e., B is hydrogen or a blocking group.

Unless otherwise qualified, reference herein to C-6' analogs of spectinomycin, includes both references to the aforementioned novel C-6' analogs and known C-6' analogs of spectinomycin shown by the formula I which C-6' analogs further includes analogs with the nitrogen atoms bonded to C-1 and C-3 blocked, i.e., B is hydrogen or a blocking group.

Blocking groups referred to above are sometimes called "protective groups" in the art and are well known in many fields of organic chemistry, including peptide chemistry, fatty acid chemistry and especially semi-synthetic and synthetic antibiotic chemistry. Two commonly used blocking groups are carbobenzyloxy and t-butoxycarbonyl. Such groups can be removed easily and replaced by hydrogen atoms with suitable treatments, which may vary in detail depending on the particular blocking group and the particular molecule to which it is bonded, with acids or by reduction. A quite comprehensive list of blocking groups which can be attached to spectinomycin analogs is disclosed in U.S. Pat. No. 4,173,647, the selection, preparation, use and removal of which is incorporated herein by reference. Regarding the chemistry of adding and removing such blocking, see. e.g., Boissona, Adv. Org. Chem. 3, 159 (1963) and Windholz et al., Tetrahedron Lett. 8, 2555 (1967).

Spectinomycin itself is a known natural product. See Bergy et al., U.S. Pat. No. 3,234,092. Numerous spectinomycin analogs in which the nitrogen atom bonded to C-1 and C-3 are blocked are also known. See White, inventor of both, U.S. Pat. Nos. 4,351,771 and 4,361,701; Federal Republic of Germany Offenlegungschriften Nos. 2,756,912 (Derwent Farmdoc Accession No. 50959B) and 2,756,913 (Derwent Farmdoc Accession No. 40960B). The White patents include numerous C-6' analogs including the 5'-desmethyl analog, of spectinomycin as well as such analogs with nitrogen atoms bonded to C-1 and C-3 blocked.

The present invention also concerns novel synthetic processes. In particular, it concerns;

(i) the novel synthesis of C-6' analogs of spectinomycin of formula I wherein $E_1$ and $E_2$ may be the same or different and are
  (a) hydrogen,
  (b) alkyl of from 1 to 8 carbon atoms, inclusive, with the proviso that only $E_2$ is alkyl,
  (c) essentially hydrocarbyl, with the proviso that only $E_2$ is hydrocarbyl,
  (d) aryl, with the proviso that only $E_2$ is aryl,
  (e) $C(O)OR_2$ wherein $R_2$ is hydrogen, alkyl of from 1 to 8 carbon atoms, inclusive, or aryl or
  (f) CN;

(ii) the novel synthesis of a novel intermediate illustrated by the formula II wherein $E_1$ and $E_2$ are as defined above; $B_1$ is a blocking group from among those blocking the nitrogen atoms bonded to C-1 and C-3 as discussed above; and $B_2$, $B_3$ and $B_4$ are oxygen protecting groups;

(iii) the novel synthesis of a novel intermediate illustrated by the formula III wherein $E_1$ and $E_2$ are as defined above; $B_1$, $B_2$, $B_3$ and $B_4$ are as defined above;

(iv) the novel synthesis of a novel intermediate illustrated by the formula IV wherein $B_1$, $B_2$, $B_3$ and $B_4$ are as defined above;

(v) the novel synthesis of a novel intermediate illustrated by the formula V wherein $B_1$, $B_2$ and $B_3$ are as defined above;

(vi) the novel synthesis of a novel N-protected actinamine having selected oxygen atom protection illustrated by the formula VI wherein $B_1$ and $B_2$ are as defined above.

Finally, the present invention also relates to the above noted novel intermediates II, III, IV, V and VI.

Oxygen protecting groups as referred to above are selected from a variety known in the practice of synthetic organic chemistry, including reactions of various dienes with suitable dienophiles, for example, as reviewed by Danishefsky, "Siloxy Dienes in Total Synthesis", Accounts of Chemical Research, vol. 14, pp. 400–6 (1981). Other examples of appropriate oxygen protecting groups for use in the present invention can be found in references as follows:

McOmie, J. F. *Protective Groups in Organic Chemistry*, Plenum Press (1973),

Green, T. W. *Protective Groups in Organic Synthesis*, Wiley (1981).

Oxygen protecting groups which can be attached as $B_2$, $B_3$ and $B_4$ in the novel intermediates of the above processes are t-butyldiphenylsilyl, t-butyldimethylsilyl, acetyl or propionyl and the like. t-Butyldiphenylsilyl is preferred as $B_2$, t-butyldimethylsilyl is preferred as $B_4$, and an acetyl group is preferred as $B_3$.

All of the intermediates of the present invention which contain one or more oxygen blocking groups are useful intermediates in processes for making successive intermediates in processes for making C-6' analogs of spectinomycin of the present invention process which contain blocking groups on the nitrogen atoms bonded to C-1 and C-3. Replacement of the blocking groups by hydrogen on the nitrogen atoms bonded to C-1 and C-3 in C-6' analogs of spectinomycin of the present invention process provides C-6' analogs of spectinomycin having the formula I which are useful as antimicrobial agents.

The present invention also includes the pharmacologically acceptable acid addition salts of the novel antimicrobial C-6' analogs of spectinomycin having the formula I' disclosed herein.

2. Prior Art

There are few references to spectinomycin analogs with modified sugar rings in the literature, and none of these involve compounds having $E'_1$ and $E'_2$ as defined for the novel analogs of the present invention. For example, see U.S. Pat. Nos. 4,351,771; 4,361,701 and 4,173,647.

Modification at the C-6' position to produce spectinomycin analogs with modified sugar rings is known. However, previously known modification does not use the novel processes or intermediates and does not disclose the novel analogs of the present invention. Such previously known modification at the C-6' position can be found in U.S. Pat. Nos. 4,351,771 and 4,361,701 as well as in U.S. application Ser. No. 449,304, filed Dec. 13, 1982, now U.S. Pat. No. 4,532,336 which is a continuation-in-part of U.S. application Ser. No. 359,723, filed March, 1982, now abandoned. The latter noted continuation-in-part application describes the now more preferred modifications at the C-6' position and is, therefore, incorporated herein by reference. Again, none of the prior disclosures of the above cited references make obvious the present invention. Particularly, these references provide no enablement for the wide variety of substituents of the present invention at the C-6' position.

An early discussion of spectinomycin chemistry by Wiley et al., "The Chemistry of Actinospectacin. IV. The Determination of the Structure of Actinospectacin", J. Am. Chem. Soc., vol. 85, pp. 2652-9, Sept. 5, 1963, includes a compound useful in the determination of the structure of spectinomycin similar to a precursor now found useful in the process to make the novel protected actinamine having the formula VI of the present invention. However, Wiley et al. make no suggestion that such a novel actinamine of formula VI is obvious or can be made and further provides no teaching which would make it obvious to try to make the novel actinamine of the present invention.

On the other hand, White et al., in "Synthesis and In Vitro Antibacterial Properties of Alkylspectinomycin Analogs", The Journal of Antibiotics, vol. XXXVI, No. 3, pp. 339-42, Mar., 1983, discuss, as presently understood, preferred alkylspectinomycin analogs which can now be made by the present invention process.

The Diels-Alder reaction is one well known in synthetic chemistry. See the textbook, March, *Advanced Organic Chemistry: Reactions, Mechanisms and Structure*, McGraw-Hill Book Company, pp. 626-636, 1968, or more recently for the Diels-Alder reactions using siloxy dienes, see Danishefsky, "Siloxy Dienes in Total Synthesis", Accounts of Chemical Research, vol. 14, pp. 406-6, 1981. Finally, more specifically, David et al. "Stereochimie de la Cycloaddition sur les Ethers Butactienyliques d'Alcook Chiraux. Derives en 4 et 6 de Glucosides Perbenzyles", Tetrahedron, vol. 34, pp. 299-304, 1978, discuss preparation of derivatives of perbenzyl glucosides from partially protected derivatives of α-D-glucose in a reaction of cycloaddition onto butadienyl ethers of chiral alcohols. However, the above disclosures in no way make obvious or suggest the use of a Diels-Alder type reaction to obtain the spectinomycin analogs having C-6' modification of the present invention.

THE INVENTION

1. Summary of the Invention

The present invention comprises:
(A) A compound of formula I'
wherein $E'_1$ and $E'_2$ may be the same or different and are as follows:
  (a) $E'_1$ is hydrogen and $E'_2$ is aryl or an essentially hydrocarbyl substituent with the proviso that the hydrocarbyl may not be aminoalkyl, hydroxy alkyl, alkoxy alkyl, and that when the substituent is haloalkyl then at least one halo atom is on a carbon of the alkyl other than the terminal carbon.
  (b) $E'_1$ and $E'_2$ are the same or different and are selected from the group consisting of hydrogen and $C(O)OR'_2$ wherein $R'_2$ is hydrogen, alkyl of from 1 to 8 carbon atoms, inclusive, or aryl, with the proviso that $E'_1$ and $E'_2$ cannot both be hydrogen or
  (c) $E'_1$ and $E'_2$ are the same or different and are hydrogen or CN with the proviso that $E'_1$ and $E'_2$ cannot both be hydrogen.
wherein B is
(a) hydrogen or
(b) a blocking group.
(B) A process for preparing a compound of formula I, wherein $E_1$ and $E_2$ may be the same or different and are
(a) hydrogen,
(b) alkyl of from 1 to 8 carbon atoms, inclusive, with the proviso that only $E_2$ is alkyl,
(c) essentially hydrocarbyl, with the proviso that only $E_2$ is hydrocarbyl,
(d) aryl, with the proviso that only $E_2$ is aryl,
(e) $C(O)OR_2$ wherein $R_2$ is hydrogen, alkyl of from 1 to 8 carbon atoms, inclusive, or aryl or
(f) CN;
wherein B is
(a) hydrogen or
(b) a blocking group
which comprises
(a) treating a compound of formula II
wherein $E_1$ and $E_2$ are as defined above, and
wherein $B_1$ is a blocking group, and
wherein $B_2$, $B_3$ and $B_4$ are oxygen protecting groups; with an oxygen deblocking agent, for example, hydrogen fluoride when the blocking group contains silicon and recovering a compound having the formula I
wherein B is a blocking group, or
(b) treating a compound of formula II
wherein $E_1$ and $E_2$, $B_1$, $B_2$, $B_3$ and $B_4$ are as defined above; with an oxygen deblocking agent, for example, hydrogen fluoride when the blocking group contains silicon and recovering a compound of formula I wherein B is a blocking group; and replacing the blocking group with hydrogen to obtain a compound of formula I
wherein B is hydrogen.

(C) A process for preparing a compound of formula II wherein $E_1$, $E_2$, $B_1$, $B_2$, $B_3$ and $B_4$ are as defined above which comprises treating a compound having the formula III wherein $E_1$, $E_2$, $B_1$, $B_2$, $B_3$ and $B_4$ are as defined above; with step (a) $Na_2CO_3$ and then step (b) m-chloroperbenzoic acid to obtain the compound of formula II.

(D) A process for preparing a compound of formula III wherein $E_1$, $E_2$, $B_1$, $B_2$, $B_3$ and $B_4$ are as defined above;
which comprises treating a compound having the formula IV
wherein $B_1$, $B_2$, $B_3$ and $B_4$ are as defined above; with a compound having the formula VII
wherein $E_1$ and $E_2$ are as defined above; in the presence of an Lewis acid catalyst such as tris(6,6,7,7,8,8,8-heptafluoro)-2,2-di-methyl-3,5-octanedionate to obtain the compound of formula III (E) A process for preparing a compound of formula IV wherein $B_1$, $B_2$, $B_3$ and $B_4$ are as defined above
which comprises treating a compound of formula V wherein $B_1$, $B_2$, $B_3$ and $B_4$ are as defined above; with an oxygen protecting group, such as t-butyldimethylsilyl triflate, in the presence of an amine base, such as triethylamine.

(F) A process for the preparation of a compound of formula V
wherein $B_1$, $B_2$, $B_3$ and $B_4$ are as defined above;
which comprises treating a compound having the formula VI
wherein $B_1$ and $B_2$ are as defined above; with 3-(acetyloxy)-4-methoxy-3-buten-2-one in the presence of p-toluenesulfonic acid and heated to the distillation temperature of essentially pure solvent, such as benzene to obtain the compound V.

(G) A process for the preparation of a compound of formula VI.
wherein $B_1$ and $B_2$ are as defined above;
which comprises
(a) treating a compound having the formula $I_1$ wherein the nitrogen atoms bonded to C-1 and C-3 are protected; in a solvent, such as methanol, with sodium methoxide and then neutralizing the solution with acetic acid to obtain a compound having the formula VIII wherein $B_1$ is as defined above;
(b) treating the compound of (a) in a solvent, such as dimethylformide with an oxygen protecting group in the presence of imidazole to obtain a compound having the formula IX
wherein $B_1$ and $B_2$ are as defined above and
(c) treating the compound of (b) in a solvent, such as methanol with acetylchloride to obtain the compound VI.

(H) A compound having the formula II
wherein $E_1$, $E_2$, $B_1$, $B_2$, $B_3$ and $B_4$ are as defined above.

(I) A compound having the formula III
wherein $E_1$, $E_2$, $B_1$, $B_2$, $B_3$ and $B_4$ are as defined above.

(J) A compound having the formula IV
wherein $B_1$, $B_2$ and $B_3$ are as defined above.

(K) A compound having the formula V
wherein $B_1$, $B_2$ and $B_3$ are as defined above.

(L) A compound having the formula VI
wherein $B_1$ and $B_2$ are as defined above.

Finally, the present invention comprises a total process beginning from the process noted above as (G) and proceeding backwards through (F), (E), (D), (C) and including the process noted above as (B). The total process is illustrated in Scheme B. It is noted that the process (B) allows recovery of the compound having the formula I wherein B is a blocking group or a hydrogen.

The definition of alkyl includes methyl ethyl, propyl, butyl, pentyl, hexyl, heptyl or octyl and isomeric forms thereof, including cycloalkyls as found in U.S. application Ser. No. 449,304, incorporated by reference above.

Aryl is phenyl unsubstituted or substituted with, for example, one or more halogen atoms; nitro; one or two alkyl groups of from 1 to 3 carbon atoms, inclusive; and alkylthio.

An essentially hydrocarbyl substituent is an alkyl as defined above, substituted so that its alkyl characteristics are substantially maintained. Preferred substituents are from among those known to be lipophilic. For example, the alkyl may be substituted by one or more halogen atoms; including perhaloalkyls, silicon containing group or alkylthio, of from one to three carbon atoms, inclusive. The preferred haloalkyls are α,α-haloalkyls or perhaloalkyls, such as trichloromethyl or trifluoromethyl.

Halo is fluoro, chloro or bromo.

The compounds of the invention within the scope of the formula I' are useful as either antimicrobial agents or intermediates in processes for synthesizing the antimicrobial agents. The compounds within the scope of formula I' which are antimicrobial agents are the compounds of formula I' wherein B substituents are not blocking groups and pharmacologically acceptable acid addition salts thereof. The compounds within the scope of the present invention which are useful as intermediates in synthetic processes to make the antimicrobial compounds of the invention are those of formula I' wherein all the substituents B are blocking groups.

The compounds having the formula I' within the scope of the invention which are useful as antimicrobial agents are microbistatic or microbicidal. These compounds are in a class of compounds having the same chemical skeleton as shown in the compound $I_1$ which are known to have the antimicrobial activity. They are, therefore, to be used in the same manner to inhibit the growth of, or eliminate, microorganisms, including gram-negative and gram-positive bacteria, from environments in which the presence of microorganisms is undesirable or harmful. While the microbistatic or microbicidal potency of the anti-microbial agents within the scope of the invention will vary against any undesirable or harmful species of microorganisms in a particular environment, each antimicrobial agent within the scope of the invention will be useful against at least one species of microorganism in at least one environment in which the presence of members of the species is harmful or undesirable.

The antimicrobial agents within the scope of the invention are useful for treating or preventing microbial, especially bacterial, infections in mammals, including humans. Additionally, it is contemplated that the antimicrobial agents within the scope of the present invention will be useful for inhibiting the growth of, or eliminating, microorganisms from environments, other than mammalian systems, in which the presence of the microorganism is undesirable or harmful.

To be effective as microbicidal or microbicidal agents in an environment, the antimicrobial compounds within the scope of this invention must be introduced into the environment, by one of several means which are well known in the art, in a quantity sufficient to inhibit the growth of, or eliminate the growth of such agents.

2. Detailed Description of the Invention

The illustrative Examples below and each of the processes noted as F, E, D, C, and B; both in the above "Summary of the Invention" and as shown in Scheme B for each of the processes so noted therein as well, and the process noted in Scheme A, describe the preparation of novel compounds and processes of the present invention. Variations from the details given herein, e.g., solvent or temperature or other reaction conditions provided in the discussion and Examples are also contemplated as part of the invention. The discussion and Examples are intended, therefore, to be illustrative, not comprehensive.

Compounds of formula VI in Scheme A are the starting materials for synthesizing all other compounds within the scope of this invention.

Generally, the step (a) shown in Scheme A is undertaken in methanol. Other organic solvents which are inert to the reactants and in which the reactants are soluble may be used as co-solvents, such as, tetrahydrofuran, dimethoxyethane or methylene chloride. Step (b) as shown in Scheme A which selectively adds oxygen protecting groups to the compounds of formula VIII is conducted in an organic solvent such as dimethylformamide or pyridine. Hydrolysis step (c) is done in aprotic solvents such as alcohols, methanol, ethanol or propanol. Steps (a) through (c) are usually conducted at about room temperature. All steps may proceed more quickly with heat.

Usual work-up procedures to obtain the compound in each step (a), (b), or (c) are followed. For example, the solution from step (a) is neutralized with, for example, acetic acid, then concentrated and chromatographed to yield compounds of formula VIII. The solution of step (b) is poured into an inert solvent in which the salts are insoluble and the mixture filtered. Then the filtrate is concentrated and chromatographed to obtain the compound having selectively protected oxygens of formula IX. Finally, the solution obtained from step (c) is concentrated and chromatographed to obtain the actinamine having formula VI with selectively protected oxygens and both the N bonded to C-1 and the N bonded to C-3 protected by blocking groups.

Following are the general procedures for the processes F, E, D, C and B.

Process F is accomplished in a manner similar to that discussed in the Chem. Ber. reference noted in the following material. The protected actinamine having the formula VI described above is dissolved in an inert organic solvent such as benzene, methylene chloride or toluene. A compound having a protective group such as acetyl or benzoyl on the α-oxygen so that the compound is 3-(acetyloxy)-4-methoxy-3-buten-2-one or 3-(benzoyloxy)-4-methoxy-3-buten-2-one, is added to the solution along with a mild organic acid such as p-toluenesulfonic acid or methanesulfonic acid. Methanol is essentially completely removed by slow elevation of the distillation temperature. Usual work-up procedures such as concentration yields a material containing a compound having the formula V.

Simultaneous protection of the remaining unprotected oxygen in a compound having the formula V and readjustment of the conjugated double bonds as shown in process E is accomplished by dissolving the compound having formula V in a nonpolar organic solvent such as diethylether. Then, triethylamine and an oxygen protecting group such as t-butyldimethylsilyl triflate is added to the solution. It may be preferable for ease of removal that this oxygen protecting group denoted as $B_3$ is the same as that resulting in the $B_2$ on the selectively protected actinamine having formula VI prepared above. Again work-up similar to process F above yields material including the compound of formula IV.

The cyclization of process D is accomplished by dissolving the material having the compound having formula IV in a solvent such as trichloromethane, methylene chloride or toluene. The compound having formula VII is added to the solution and the progress of the reaction monitored by PMR assay for the disappearance of the vinyl protons in the compound of formula IV. If at least one of $E_1$ and $E_2$ is H then the progress of the reaction may also be monitored by the disappearance of this aldehydic proton. For a reaction in which at least one of $E_1$ and $E_2$ is H, a catalyst such as tris(6,6,7,7,8,8,8-heptafluoro)-2,2-dimethyl-3,5-octanedionate facilitates the reaction and, therefore is in this case preferred. Otherwise, heat may be added to increase the speed and completeness of the reaction.

At this time the reaction material having a compound of the formula III may be concentrated. However, the procedure may use the crude material resulting from the process noted as C herein before. The material is cooled, powdered $Na_2CO_3$ is added followed by addition of m-chloroperbenzoic acid. Again the progress of the reaction is monitored to observe the disappearance of the reactant having the formula III which absorbs 1% aqueous potassium permanganate spray reagent.

Again the reaction material having the compound, an epoxide, of the formula II resulting from the above process C may be concentrated in the reaction material but the procedure may treat the material itself from process C in the manner shown by process B herein. In the process denoted as B the crude epoxide of formula II is diluted with acetonitrile at about 0° to which mixture is added 48% aqueous hydrogen fluoride. The reaction mixture is stirred and its progress again monitored by TLC and judged against reference standards such as are found in the reference above by White et al., for example.

Final conversion to compounds having the formula I which are useful as antibacterials; i.e., compounds of formula I wherein B is hydrogen, are obtained by removal of the blocking groups on the nitrogens bonded to C-1 and C-3 of formula I. Generally, conversion and separation of compounds having formula I is accomplished in a manner similar to that described in various references cited above.

The novel compounds having the formula I' of the present invention can be used for the purpose and in the manner described in the previous references incorporated by reference for compounds of formula I known heretofore.

EXAMPLE I

Compound of formula VIII wherein $B_1$ is benzyloxycarbonyl

N,N'-bisbenzyloxycarbonyl spectinomycin [J. Amer. Chem. Soc., vol. 85, 2657 (1963)], 25 gram is dissolved in methanol (500 ml) and 25% sodium methoxide solution (20 ml) added. After 2 hours at room temperature, the solution is neutralized with acetic acid, concentrated and chromatographed to give the compound VIII wherein $B_1$ is benzyloxycarbonyl.

EXAMPLE II

Compound of formula IX wherein $B_1$ is benzyloxycarbonyl and $B_2$ is t-butyldiphenylsilyl The ester VIII from Example I (10 mmole) is dissolved in dimethylformamide (20 ml). Imidazole (50 mmole) and t-butyldiphenylsilyl chloride (20 mmole) are added and heated to 60°. The mixture is poured into toluene (10 ml), filtered and the filtrate concentrated and chromatographed to obtain the disilylester IX wherein $B_1$ is benzyloxycarbonyl and $B_2$ is t-butyldiphenylsilyl.

EXAMPLE III

Compound of formula VI wherein $B_1$ is benzyloxycarbonyl, and $B_2$ is t-butyldiphenylsilyl The disilylester IX from Example II (10 mmole) is dissolved in methanol (60 ml) and acetylchloride (2.0 ml) is added and allowed to stand at room temperature for four days. The solution is concentrated and chromatographed to obtain the disilylated actinamine VI wherein $B_1$ is benzyloxycarbonyl, and $B_2$ is t-butyldiphenylsilyl.

EXAMPLE IV

Compound of formula V wherein $B_1$ is benzyloxycarbonyl, $B_2$ is t-butyldiphenylsilyl, and $B_3$ is acetyl The disilylated actinamine VI from Example III (10 mmole) is dissolved in benzene (150 ml). 3-(Acetyloxy)-4-methoxy-3-buten-2-one (10 mmole, Chem. Ber. 92, 3009, 1959) is added along with p-toluenesulfonic acid (0.05 g). The solution is heated to remove methanol, the progress of the reaction being followed by elevation of the distillation temperature to that of essentially pure benzene. The solution is then concentrated and the enone V wherein $B_1$ is benzyloxycarbonyl, $B_2$ is t-butyldiphenylsilyl, and $B_3$ is acetyl is isolated by chromatography.

EXAMPLE V

Compound of formula IV wherein $B_1$ is benzyloxycarbonyl, $B_2$ is t-butyldiphenylsilyl, and $B_3$ is acetyl, and $B_4$ is t-butyldimethylsilyl Enone V of Example IV (1 mmole) is dissolved in diethylether (10 ml). Triethylamine (1.1 mmole) and t-butyldimethylsilyl triflate (Fluka) (1 mmole) is added. The salts are filtered and the filtrate is concentrated and chromatographed to yield diene IV wherein $B_1$ is benzyloxycarbonyl, $B_2$ is t-butyldiphenylsilyl, $B_3$ is acetyl, and $B_4$ is t-butyldimethylsilyl.

EXAMPLE VI

Compound III wherein $E_1$ is hydrogen, $E_2$ is n-butyl, $B_1$ is benzyloxycarbonyl, $B_2$ is t-butyldiphenylsilyl, $B_3$ is acetyl, and $B_4$ is t-butyldimethylsilyl The diene IV of Example V (1 mmole) is dissolved in $CDCl_3$ or $CHCl_3$ (6 ml) and the aldehyde $E_2CHO$ wherein $E_2$ is alkyl, preferably n-butyl (1 mmole) is added as is tris(6,6,7,7,8,8,8-heptafluoro, 2,2-dimethyl-3,5-octanedionate) europium (0.02 mmole, Aldrich). The progress of the reaction is followed by PMR assay for the disappearance of vinyl protons in diene IV as well as aldehydic proton of RCHO. The title Compound III is obtained wherein $E_1$ is hydrogen, $E_2$ is n-butyl, $B_1$ is benzyloxycarbonyl, $B_2$ is t-butyldiphenylsilyl, $B_3$ is acetyl, and $B_4$ is t-butyldimethylsilyl. At this time the crude material is processed in the following step.

EXAMPLE VII

Compound II wherein $E_1$ is hydrogen, $E_2$ is n-butyl, $B_1$ is benzyloxycarbonyl, $B_2$ is t-butyldiphenylsilyl, $B_3$ is acetyl, and $B_4$ is t-butyldimethylsilyl Crude enantiomeric III of Example VI (1 mmole) in $CDCl_3$ (or $CHCl_3$) is cooled to 0° and dried, powdered $Na_2CO_3$ (100 mg) is added followed by m-chloroperbenzoic acid (1 mmole). The reaction is monitored by TLC (using 1:9 $CH_3CN$—$CHCl_3$) disappearance of the spot IV which absorbs 1% aq. potassium permanganate spray reagent. At this time the material which now contains Compound II wherein $E_1$ is hydrogen, $E_2$ is n-butyl, $B_1$ is benzyloxycarbonyl, $B_2$ is t-butyldiphenylsilyl, $B_3$ is acetyl, and $B_4$ is t-butyldimethylsilyl is processed in the next desilylation step.

EXAMPLE VIII

Compound I wherein $E_1$ is hydrogen, $E_2$ is n-butyl

The crude epoxide II of Example VII is diluted with 0° acetonitrile (10 ml) and 48% aq. HF (3.0 ml) is added with magnetic stirring at 0°. Reaction progress is monitored by TLC. In many cases complete conversion to these products can be judged wth reference standards (The Journal of Antibiotics, p. 339 (1983)). Conversion of compounds I wherein B is carbobenzyloxycarbonyl to antibacterial compounds has been described. (The Journal of Antibiotics, p. 339 (1983)).

SCHEME A

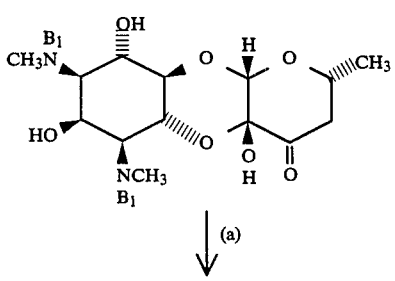

-continued
SCHEME A
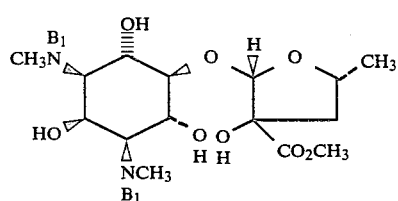  VIII
↓ (b)
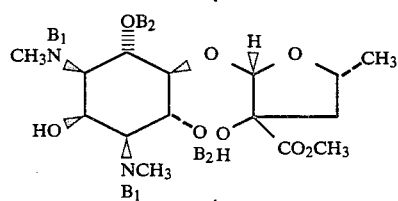  IX
↓ (c)
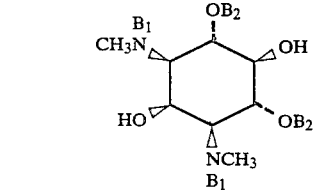  VI
SCHEME B
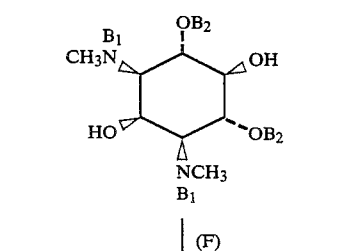  VI
↓ (F)
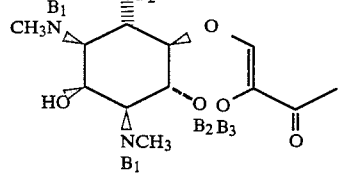  V
↓ (E)
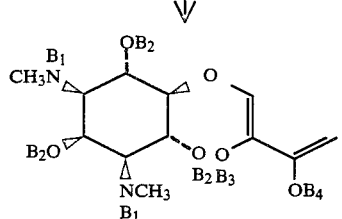  IV
↓ (D)
-continued
SCHEME B
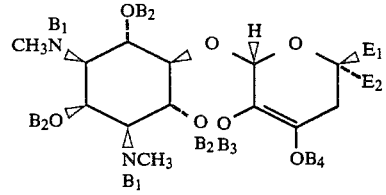  III
↓ (C)
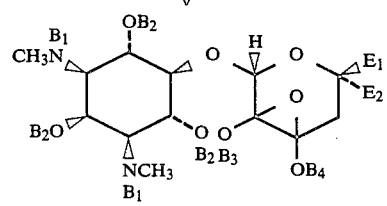  II
↓ (B)
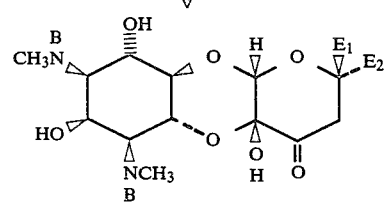  I
FORMULA
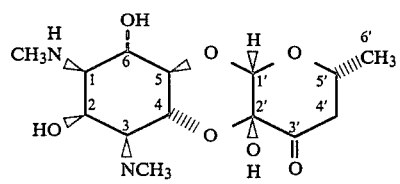  $I_1$
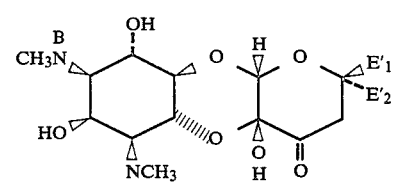  I'
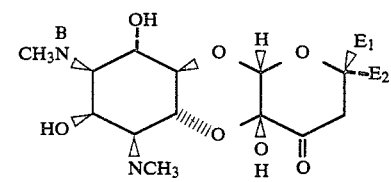  I
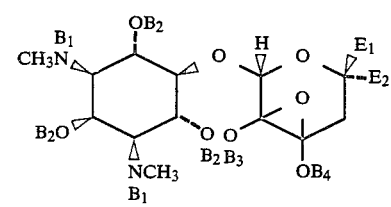  II -continued
FORMULA

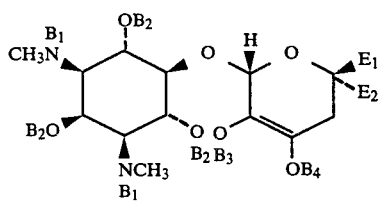

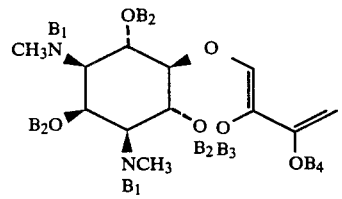

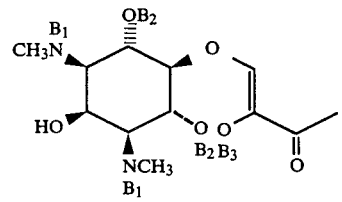

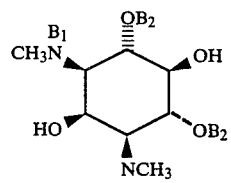

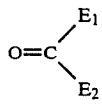

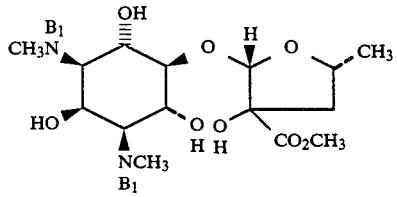

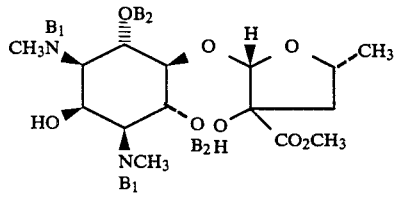

I claim:
1. A compound of

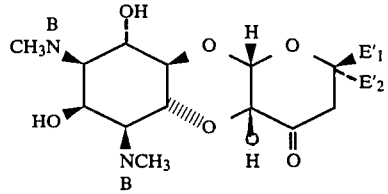

wherein $E'_1$ and $E'_2$ may be the same or different and are (a) $E'_1$ is hydrogen and $E'_2$ is aryl or alkyl substituted by at least one silicon containing group or alkylthio of 1 to 3 carbon atoms;

(b) $E'_1$ and $E'_2$ are the same or different and are selected from the group consisting of hydrogen and $C(O)OR'_2$ wherein $R'_2$ is hydrogen, alkyl of from 1 to 8 carbon atoms, inclusive, or aryl, with the proviso that $E'_1$ and $E'_2$ cannot both be hydrogen or (c) $E'_1$ and $E'_2$ are the same or different and are hydrogen or CN with the proviso that $E'_1$ and $E'_2$ cannot both be hydrogen;

wherein B is
(a) hydrogen or
(b) a blocking group.

2. A compound according to claim 1 wherein the alkyl is substituted by at least one silicon containing group or alkylthio, of from 1 to 3 carbon atoms.

3. A compound according to claim 1 wherein $E'_1$ and $E'_2$ are the same or different and are hydrogen; $C(O)OR'_2$ wherein $R'_2$ is hydrogen, alkyl of from 1 to 8 carbon atoms, inclusive, or aryl; and CN with the overall proviso that both $E'_1$ and $E'_2$ are not both hydrogen.

4. A process for preparing a compound of formula

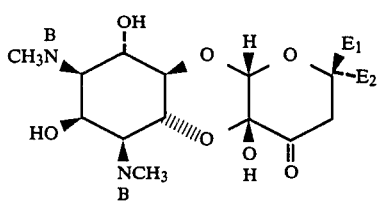

wherein $E_1$ and $E_2$ are the same or different and are
(a) hydrogen,
(b) alkyl of from 1 to 8 carbon atoms, inclusive, with the proviso that only $E_2$ is alkyl,
(c) essentially hydrocarbyl, with the proviso that only $E_2$ is hydrocarbyl,
(d) aryl, with the proviso that only $E_2$ is aryl,
(e) $C(O)OR_2$ wherein $R_2$ is hydrogen, alkyl of from 1 to 8 carbon atoms, inclusive, or aryl or
(f) CN;

wherein B is
(a) hydrogen or
(b) a blocking group which comprises
  (a) treating a compound of formula

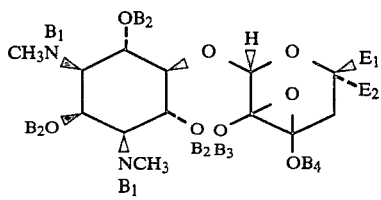

wherein $E_1$ and $E_2$ are as defined above;

wherein $B_1$ is a blocking group; and wherein $B_2$, $B_3$ and $B_4$ are oxygen protecting groups; with an oxygen deblocking agent and recovering a compound having the formula I.

5. A process for preparing the compound I according to claim 4 wherein $E_2$ is alkyl of from 1 to 8 carbon atoms, inclusive.

6. A process for preparing the compound I according to claim 4 wherein $E_2$ is a substituted alkyl.

7. A process according to claim 5 wherein the alkyl is substituted by one or more halogen atoms; silicon containing group or alkylthio of from 1 to 3 carbon atoms, inclusive.

8. The process according to claim 6 wherein the substituted alkyl is $\alpha,\alpha$-haloalkyl or perhaloalkyls.

* * * * *